United States Patent [19]

Grinberg et al.

[11] Patent Number: 4,500,516

[45] Date of Patent: Feb. 19, 1985

[54] ANTIBACTERIAL PHARMACEUTICAL COMPOSITION

[75] Inventors: Grigory M. Grinberg, Moscow; Oleg N. Akifiev, Riga; Jury A. Pytel, Moscow; Anatoly P. Gilev; Monika Y. Paberza, both of Riga, all of U.S.S.R.

[73] Assignee: Institut Organicheskogo Sinteza Akademii Nauk Latviiskoi SSR, Riga, U.S.S.R.

[21] Appl. No.: 436,019

[22] Filed: Oct. 22, 1982

[51] Int. Cl.³ .............................................. A61K 33/10
[52] U.S. Cl. .................................................... 424/156
[58] Field of Search ............................ 424/156, 273 R

[56] References Cited

U.S. PATENT DOCUMENTS 3,531,477  9/1970  Giller et al. ......................... 424/273
3,644,344  2/1972  Mousseron et al. ................. 424/273

FOREIGN PATENT DOCUMENTS 1129195 10/1968 United Kingdom .

*Primary Examiner*—Allen J. Robinson
*Assistant Examiner*—John W. Rollins
*Attorney, Agent, or Firm*—Ladas & Parry

[57] ABSTRACT

Disclosed is an antibacterial pharmaceutical composition comprising potassium salt of N-[$\beta$-(5'-nitrofuryl-2')-acrylidene]-1-aminohydantoin and basic magnesium carbonate in conjunction with a pharmaceutically suitable filler.

The proposed antibacterial pharmaceutical composition has a broader spectrum of action and a higher biological accessibility than the other antibacterial pharmaceutical compositions of the nitrofuran series known in the prior art. The proposed pharmaceutical composition is considerably less toxic than the prior-art antibacterial pharmaceutical compositions of the nitrofuran series and affords a bacteriostatic effect exceeding appreciably that of the prior-art antibacterial pharmaceutical compositions of the nitrofuran series.

6 Claims, No Drawings

ANTIBACTERIAL PHARMACEUTICAL COMPOSITION

FIELD OF THE INVENTION

The present invention is in the field of medicine. More specifically, it relates to antibacterial pharmaceutical compositions containing compounds of the nitrofuran series.

One end use in which the present invention can be most successful is as an antibacterial agent to be employed for treating various infectious inflammatory diseases, such as sepsis, infectious urologic diseases, pancreatitis, infectious inflammatory diseases of the lungs (chronic bronchites, pneumonias, or bronchiectases), including such as may be further complicated by infectious allergic bronchial asthma.

In addition, the present invention can also be useful as an antibacterial agent to prevent inflammatory complications.

BACKGROUND OF THE INVENTION

One pharmaceutical composition widely known to the prior art as an antibacterial agent of the nitrofuran series is 1-(5'-nitrofurfurylideneamino)-hydantoin having the following structural formula $$\begin{array}{c} HC\text{———}CH \\ \parallel \quad\quad \parallel \\ O_2NC \quad\quad C-CH=N-N\text{———}C=O \\ \diagdown O \diagup \quad\quad\quad | \quad\quad | \\ \quad\quad\quad H_2-C \quad N-H \\ \quad\quad\quad\quad \diagdown C \diagup \\ \quad\quad\quad\quad\quad \parallel \\ \quad\quad\quad\quad\quad O \end{array}$$

and trade named as Nitrofurantoin and Furadantin.

Said pharmaceutical composition is quickly absorbable from the gastrointestinal tract, with the drug concentration in the blood and in the urine capable of reaching a level sufficient to produce a therapeutic effect.

Said pharmaceutical composition is easy to use in medical practice under conditions of both hospital and outpatient treatment, considering that it is designed for oral administration (as capsules, tablets, or suspension).

However, said pharmaceutical composition has a relatively limited spectrum of action, being used in practical medicine for the theory of infectious urologic diseases only.

Also, said pharmaceutical composition is noticeably toxic. In the case of oral administration to white mice, $LD_{50}$ is 166.7 mg/kg.

Sometimes this pharmaceutical composition is observed to meet with intolerance.

The bacteriostatic concentration value for this pharmaceutical composition is comparatively high, and this, coupled with the considerable level of toxicity of the drug, will frequently restrict its usage in medical practice.

Besides, said pharmaceutical composition is quickly removed from the organism.

Another pharmaceutical composition widely known in the prior art as an antibacterial agent of the nitrofuran series is N-[β-(5'-nitrofuryl-2')-acrylidene]-1-aminohydantoin having the following structural formula:

$$\begin{array}{c} HC\text{———}CH \\ \parallel \quad\quad \parallel \\ O_2N-C \quad\quad C-CH=CH_2-CH=N-N\text{———}C=O \\ \diagdown O \diagup \quad\quad\quad\quad\quad\quad\quad | \quad\quad | \\ \quad\quad\quad\quad\quad\quad\quad H_2-C \quad N-H \\ \quad\quad\quad\quad\quad\quad\quad\quad \diagdown C \diagup \\ \quad\quad\quad\quad\quad\quad\quad\quad\quad \parallel \\ \quad\quad\quad\quad\quad\quad\quad\quad\quad O \end{array}$$

and commercialized under the trade name of Furagin.

This pharmaceutical composition possesses a wider spectrum of therapeutic action than the aforesaid Nitrofurantoin and Furadantin. Apart from being used for the treatment of infectious urologic diseases, it can be utilized, in particular, as an antibacterial agent for the treatment of wounds and purulent infections.

With oral administration of said pharmaceutical composition, the drug concentration in the urine will reach a level sufficient to give a therapeutic effect.

The bacteriostatic concentration of Furagin for various aspects of pathogenic microorganisms is 10 to 20 times lower than the respective value for Nitrofurantoin.

Besides, said pharmaceutical composition is less toxic than Nitrofurantoin or Furadantin.

However Furagin is but very poorly soluble in water. This puts a limitation on its use by injection and, in particular, by intravenous administration, as also on its being used, as ampouled solution, for treating operating fields.

Also, in quite a number of cases, said pharmaceutical composition is observed to meet with intolerance.

A further pharmaceutical composition known to the prior art as an antibacterial agent of the nitrofuran series is potassium salt of N-[β-(5'-nitrofuryl-2')-acrylidene]-1-aminohydantoin having the following structural formula $$\begin{array}{c} H-C\text{———}C-H \\ \parallel \quad\quad \parallel \\ O_2N-C \quad\quad C-CH=CH_2-CH=N-N\text{———}C=O \\ \diagdown O \diagup \quad\quad\quad\quad\quad\quad\quad | \quad\quad | \\ \quad\quad\quad\quad\quad\quad\quad H_2-C \quad N-K \\ \quad\quad\quad\quad\quad\quad\quad\quad \diagdown C \diagup \\ \quad\quad\quad\quad\quad\quad\quad\quad\quad \parallel \\ \quad\quad\quad\quad\quad\quad\quad\quad\quad O \end{array}$$

and commercialized under the trade name of Solafur (see U.K. Pat. No. 1,129,195).

Solafar is an antibacterial agent of a broader spectrum of action compared to Furagin. The drug retains its activity with reference to such pathogenic strains of staphylococci and a number of such microorganisms as are resistant to other chemotherapeutic agents and antibiotics. Also, microorganisms will develop practically no drug resistance to Solafur. One characteristic feature of said pharmaceutical composition is its capability of producing synergistic action with a range of antibiotics upon most pathogenic microorganisms.

Solubility of Solafur in water is higher than that of the aforementioned Furagin, and this favours its administration by injection and its use for treating operating fields.

Said pharmaceutical composition is used in medical practice as 0.1% isotonic solution administered by injection and, specifically, by intravenous injection.

However, when the desired drug concentration in the blood is higher than the bacteriostatic value, the Solafur solution is to be administered intravenously by the drop method and in large quantities.

A faster method of administration used with this drug will cause headache and nausea.

Besides, in some cases this pharmaceutical composition is observed to meet with intolerance.

Administration of pharmaceutical compositions by injection and, more particularly, by intravenous injection, puts certain limitations on their use in the treatment of outpatients.

The instability in storage characteristic of aqueous solutions of Solafur makes it necessary to prepare solutions ex tempore, immediately before use.

In the case of oral administration to white mice, $LD_{50}$ of Solafur amounts to 390 mg/kg.

Considering the fact that Furagin is an acid (pK=6) and is capable of forming salts, administration of its potassium salt, i.e. Solafur, by injection has been deemed unsuitable by those skilled in the art, inasmuch as, the pH inside the stomach being generally within 1 to 3, those skilled in the art were of the opinion that the effect of the acid environment of the stomach would be to convert Solafur to the parent Furagin whose action would actually determine the therapeutic effect of the pharmaceutical composition used.

Investigations carried out on excretions of Furagin and Solafur following oral adminstration to rabbits weighing 2.8 to 3.5 kg of said pharmaceutical compositions in 5 mg/kg dosages, have demonstrated that over the first 4 hours after administration the concentrations of said compounds in the urine are roughly equal. The total quantity of Furagin removed over a period of 48 hours amounts to 2.75±0.41% of the total quantity of the pharmaceutical composition administered. For Solafur, respectively, this quantity is equal to 2.83±0.48% of the total quantity of Solafur administered.

In view of the reasons stated above, Solafur is used in medical practice for injections only.

SUMMARY OF THE INVENTION

It is an object of the present invention to provide an antibacterial pharmaceutical composition comprising potassium salt of N-[β-(5'-nitrofuryl-2')-acrylidene]-1-aminohydantoin as one of its active constituents that would possess, when orally administered, high biological accessibility.

Another object of the present invention is to provide an antibacterial pharmaceutical composition comprising potassium salt of N-[β-(5'-nitrofuryl-2')-acrylidene]-1-aminohydantoin as one of its active constituents that would feature, when orally administered, high bacteriostatic effect.

Still another object of the present invention is to provide an antibacterial pharmaceutical composition comprising potassium salt of N-[β-(5'-nitrofuryl-2')-acrylidene]-1-aminohydantoin as one of its active constituents that would feature, when orally administered, low toxicity.

Yet another object of the present invention is to provide an antibacterial pharmaceutical composition comprising potassium salt of N-[β-(5'-nitrofuryl-2')-acrylidene]-1-aminohydantoin as one of its active constituents that would possess a broad spectrum of therapeutic action when orally administered.

With these and other objects in view, there is provided a pharmaceutical composition comprising potassium salt of N-]β-(5'-nitrofuryl-2')-acrylidene]-1-aminohydantoin and basic magnesium carbonate in conjunction with a pharmaceutically suitable filler.

The proposed pharmaceutical composition will hereinafter be referred to as Furamag.

Contrary to all expectations, we have established that when Furamag is administered orally its biological accessibility is 3 times as high as that of Solafur.

Also, the Furamag concentration in the urine is 58 times that of the bacteriostatic value as early as 15 minutes after the administration, the Furamag concentration in the blood, after the first 15 minutes, being twice as high as that of Solarfur (at identical dosages).

In the case of oral administration of Furamag to white mice, $LD_{50}$ amounts to 1400 mg/kg, which is 3.5 times less than the respective value for Solafur and 8.3 times less than the respective value for Nitrofurantoin when administered to white mice by the same method.

No side effects are observable when Furamag is administered orally.

The observations made so far enable a conclusion to the effect that Furamag has a different mechanism of action compared to Solafur: being absorbed from the gastrointestinal tract, Furamag builds up to a high bacteriostatic concentration in the veins feeding the portal vein of the liver, eliminating the bacteriemia and thereby improving the immunological condition of the organism.

DETAILED DESCRIPTION OF THE INVENTION

The proposed composition can be prepared as follows.

Into a sigma-bladed mixer are introduced in succession, with stirring, potassium carbonate and water to form a solution, into which are then added N-[β-(5'-nitrofuryl-2')-acrylidene]-1-aminohydantoin and basic magnesium carbonate to form a homogeneous mass which is subsequently granulated and the granules obtained are dried. The dry granulate is screened, dusted in a cube mixer with talc, and packed into lidded hard-gelatin capsules (capsulae operculatae).

The invention will now be described with reference to the following illustrative Example.

EXAMPLE

Into a sigma-bladed mixer are introduced in succession, with stirring, 69.105 g (0.5 mole) of potassium carbonate and 0.2 l of water to form a solution, into which are then added 264.2 g (1 mole) of N-[β-(5'-nitrofuryl-2')-acrylidene]-1-aminohydantoin and 302.3 g of basic magnesium carbonate to form a homogeneous mass which is subsequently granulated by passing through a screen No. 1.6 and a screen No. 0.63, and the granules obtained are dried. The dry granulate is screened by passing through a screen No. 0.63, dusted in a cube mixer with 18.7 g (3%) of talc, and packed into lidded hard-gelatin capsules (capsulae operculatae).

The pharmaceutical composition thus obtained contains 48.5% of N-[β-(5'-nitrofuryl-2')-acrylidene]-1-aminohydantoin, 48.5% of basic magnesium carbonate, and 3% of talc.

BIOLOGICAL INVESTIGATIONS

Investigation 1

Investigation of the proposed pharmaceutical composition for biological accessibility was carried out in anesthetized rabbits, administering the said pharmaceutical composition intraduodenally.

The proposed pharmaceutical composition prepared as described in the above Example was administered in a dose of 100 mg/kg.

The maximum concentration of potassium salt of N-[β-(5'-nitrofuryl-2')acrylidene]-1-aminohydantoin in the urine was reached by 60 minutes and amounted to 92 mg%. Investigation 2 (for comparison)

Furadantin was investigated for biological accessibility in anesthetized rabbits, the drug being administered intraduodenally in a dose of 50 mg/kg based on Nitrofurantoin.

The maximum Furadantin concentration in the urine was reached by 60 minutes and amounted to 61 mg %.

Investigation 3

Investigation of the proposed pharmaceutical composition for biological accessibility was carried out in breedless rabbits having a bodymass of 3.0 to 3.5 kg and which had been starved for 24 hours before being given their standard feed prior to the commencement of the experiment.

The proposed pharmaceutical composition prepared as described in the above Example was administered orally in a dose of 100 mg/kg.

The total excretion of the proposed pharmaceutical composition with urine was 9.31±1.00 mg over a period of 24 hours.

Investigation 4 (for comparison)

Solafur was investigated for biological accessibility in breedless rabbits having a bodymass of 3.0 to 3.5 kg and which had been starved for 24 hours before being given their standard feed prior to the commencement of the experiment.

Solafur was administered in a dose of 50 mg/kg.

The total excretion of Solafur with urine was 3.43±0.3 mg over a period of 24 hours.

Investigation 5

Anesthetized rabbits were given intraduodenally the pharmaceutical composition prepared as described in the above Example in a dose of 100 mg/kg.

15 minutes after the administration of the drug, the concentration of potassium salt of N-[β-(5'-nitrofuryl-2')-acrylidene]-1-aminohydantoin was equal to 17 mg % in the urine and 0.54 mg % in the blood.

The bacteriostatic concentration of potassium salt of N-[β-(5'-nitrofuryl-2')-acrylidene]-1-aminohydantoin was found equal to 0.25 mg % for such pathogenic species of microorganisms as, for example, *Staphylococcus aureus haemolyticus, Bac. mycoides,* or *Bac. coil.*

Investigation 6 (for comparison)

When 0.1 % Solafur solution is administered by the drop method to anesthetized rabbits, the drug concentration in the blood reaches 0.28 mg % 15 minutes after the commencement of administration.

CLINICAL INVESTIGATIONS

Investigated were capsules containing each 100 mg of Furamag prepared as described in the illustrative Example.

Case 1

Patient Sh., aged 85. Had been treated for acute gangrenous cholecystitis. A cholecystectomy was performed. Kefsol and penicillin were used initially in the postoperative period. But starting from the 8th day, when the patient's temperature was still subfebrile, administration of capsuled Furamag was commenced, one capsule four times a day. A good therapeutic effect was to be observed. The wound healed over by first intention. The patient's temperature was normalized. All symptoms of inflammation disappeared. The patient left the hospital in a satisfactory condition on the 19th day.

Case 2

Patient G, aged 41. A cholecystectomy was performed. Administration of Furamag was commenced, two capsules twice a day, in the postoperative period, starting from the 6th day, while still at a subfebrile temperature. Inflammatory symptoms gradually disappeared. The wound healed over by first intention. The patient left the hospital on the 14th day.

Case 3

Patient Kh., aged 31. A laparotomy was performed, with drainage provided from the purulent cyst of the pancreas. Furamag was aministered, two capsules twice a day, from the 12th to the 19th day of the postoperative period. Suppuration from the cyst of the pancreas disappeared. The would closed over, with granulation. There were no longer any clinical or laboratory evidence of inflammatory symptoms to be observed. The patient left the hospital on the 28th day.

Case 4

Patient G., aged 36. Diagnosis: acute pancreatitis, diffuse peritonitis. Had used, over a long period, conventional drugs (antibiotics, sulphonylamides, spasmolytic agents). No improvement had been reached. The blood picture showed septic changes.

Administration of Furamag began on the 5th day, two capsules thrice a day. On the second day from the beginning of treatment, the general intoxication showed a decrease. The general condition improved on the 4th day. The blood picture showed less septic symptoms. Discharges from the wound, previously purulent, became serous. Bacteriologically, the conditions were sterile. On the 6th day the blood picture was normalized. The general condition improved appreciably. There were no symptoms of intoxication in evidence. A recovery period commenced. On the 12th day the patient was transferred from the intensified therapy ward to the surgical department.

Case 5

Patient Z., aged 52. Diagnosis: acute cholecystitis. Had been treated with antibiotics and spasmolytic agents. No improvement had been reached. The general condition had continued to aggravate.

Surgery was suggested as the only method of treatment. Yet it was finally decided to begin with Furamag therapy. On the second day after Furamag therapy was commenced (two capsules thrice a day), there were improvements in local symptoms. There were no more pains. Inflammatory symptoms were less pronounced in the blood picture. On the 4th day the blood picture normalized. There was no fever. No pains. Recovery was actually taking place.

Case 6

Patient S., aged 26. Diagnosis: peritonitis following an acute appendicitis operation. The operation had been made to late, thus giving rise to peritonitis.

Furamag therapy was commenced (two capsules thrice a day). On the 3rd day after the commencement of therapy, the patient's condition was improved, and the blood picture normalized. Liquid discharges from the abdominal cavity decreased. A tendency was observed for the intestinal fistula to close. A bacteriological investigation of the secretion from the wound showed the conditions to be sterile.

On the 6th day after the commencement of therapy, the intestinal fistula was closed. The patient was transferred from the intensified therapy ward to the surgical department.

Case 7

Patient Kh., aged 40. Diagnosis: bronchial asthma (infectious allergic form), bronchiectasis with chronic purulent intoxication and concomitant pyelonephritis. Furamag therapy was undertaken for the duration of 14 days (two capsules thrice a day).

Drug efficiency was evaluated by way of clinical, laboratory and endoscopic investigations of the patient, dynamics thereof, prior to and after the Furamag therapy.

An improvement was to be observed in the patient's general state of health, with less coughing and less sputum, the nature of sputum changing from purulent to crudum. On completion of the Furamag therapy, the blood count was found to be normalized, and a noticeable tendency was observed towards a reduced quantity of sialic acids and haptoglobin in the blood serum.

It has thus been established that Furamag possesses a broad spectrum of therapeutic action. Specifically, it can be used for treating pancreatitis, infectious inflammatory diseases of the lungs, even in cases complicated by infectious allergic bronchial asthma, infectious urologic diseases, and peritonitis. Furamag can also be useful as an antibacterial agent for the prevention of inflammatory complications.

Furamag has a considerably higher biological accessibility than the prior-art antibacterial agents of the nitrofuran series.

Furamag concentration in the blood and in the urine will quickly reach a level substantially higher than the bacteriostatic value, while using dosages customarily used with drugs of the nitrofuran series.

Furamag will give a bacteriostatic effect exceeding that produced by intravenous infusion of Solafur administered by the drop method.

Furamag is appreciably less toxic than the prior-art antibacterial agents of the nitrofuran series.

No side effects or drug intolerance have been revealved while studying Furamag under clinical conditions.

We claim:

1. An antibacterial composition comprising an antibacterially effective amount of an active agent consisting of the potassium salt of N-[$\beta$-(5'-nitrofuryl-2')-acrylidene]-1-amino hydantoin and an equivalent amount by weight of basic magnesium carbonate, in combination with a pharmaceutically acceptable filler.

2. A composition according to claim 1, wherein said filler is talc and comprises about 3% by weight of said composition.

3. A composition according to claim 1, in unit dosage form for oral administration at a dosage of about 100 mg per unit.

4. A method of treating infectious bacterial inflammatory diseases and preventing inflammatory complications, comprising administering to a human or animal patient an antibacterially effective amount of a composition according to claim 1.

5. A method according to claim 4, wherein said effective amount in humans comprises between about 400 mg and 600 mg per day in oral unit dosage form.

6. A method of preparing an antibacterial composition, comprising forming a solution of potassium carbonate in water at a ratio of 0.2 l of water per 0.5 mole of potassium carbonate, mixing 1 mole of N-[$\beta$-(5'-nitrofuryl-2')-acrylidene]-1-aminohydantoin and 302.3 g of basic magnesium carbonate per 69.105 g mole of potassium carbonate into said solution to form a homogeneous mass; granulating said homogeneous mass; drying the resultant granules; and combining an antibacterially effective amount of said granules with a pharmaceutically acceptable filler.

* * * * *